United States Patent [19]

Christiansen

[11] 4,384,586
[45] May 24, 1983

[54] METHOD AND APPARATUS FOR PH RECORDING

[76] Inventor: Torben F. Christiansen, Vejlesøparken 27, DK-2840 Holte, Denmark

[21] Appl. No.: 139,773

[22] Filed: Apr. 14, 1980

Related U.S. Application Data,

[63] Continuation of Ser. No. 12,847, Feb. 16, 1979, abandoned.

[30] Foreign Application Priority Data

Feb. 17, 1978 [DK] Denmark ............................ 727/78

[51] Int. Cl.³ ............................................ A61B 5/00
[52] U.S. Cl. .................................... 128/635; 204/403
[58] Field of Search ............................ 128/632–635; 204/195 B

[56] References Cited

U.S. PATENT DOCUMENTS 3,838,682 10/1974 Clark et al. ........................ 128/635
4,005,700 2/1977 Parker ................................ 128/632

OTHER PUBLICATIONS

Vallbona et al., "Computer Analysis . . . Acid–Base Status", Computers-Bio-Med. Res. 4, No. 6, 623–633, 1971.

Primary Examiner—Lee S. Cohen
Attorney, Agent, or Firm—Hubbell, Cohen, Stiefel & Gross

[57] ABSTRACT

For continuous or intermittent monitoring or recording of the in vivo plasma pH of a patient, the patient's acid base status is established with performance of at least one in vitro determination on a blood sample from the patient, and for a period of some hours thereafter, the patient's in vivo plasma pH is determined on the basis of this initial acid base status and the results of non-invasive measurements of the patient's actual blood $P_{CO_2}$.

16 Claims, 7 Drawing Figures

METHOD AND APPARATUS FOR PH RECORDING

This is a continuation of application Ser. No. 12,847, filed Feb. 16, 1979, now abandoned.

The present invention concerns a method and an apparatus for continuous or intermittent monitoring of pH in a patient's blood or plasma, below called the patient's "in vivo plasma pH".

In various clinical situations, it is important to have continuous information about the patient's in vivo plasma pH over a period. Thus, it is known that children seldom survive a decrease in in vivo plasma pH to below 6.8, and that on the whole a decrease in pH has many significant effects, including stimulation of the periferic and central chemoreceptors, increase in the plasma concentration of potassium, increase in the plasma phosphate concentration and decrease in the intracellular concentration of organic phosphates, a considerable increase of the plasma concentration of adrenaline and nor-adrenaline, and an increase of the blood pressure. Vasodilatation in the brain, which is probably due to a decrease in the pH of the extracellular brain liquor, causes an increased blood flow in the brain and an increased intracranial pressure with headache and, at last, coma as symptoms. The therapy in the case of dangerously low pH values is, for example, artificial ventilation. In recent years, also infusion of sodium bicarbonate has been used for correcting a dangerously low pH in new-borns. A too high plasma pH may also result in a dangerous condition and may, for example, increase the protein binding of $Ca^{++}$ resulting in a decrease of free ionized calcium which may lead to muscle fibrillations and even tetanus.

In the known art, a monitoring of a patient's in vivo plasma pH may be obtained either by withdrawing blood samples from the patient at the times desired, or by using a transcutaneous pH electrode of the kind described for example in U.S. Pat. No. 4,033,330, or a measuring chamber for determining electromagnetic radiation of the kind disclosed in U.S. Pat. No. 4,041,932. The former method permits only the obtainment of "instantaneous pictures" at the time of the blood sample withdrawal, and another disadvantage is that the patient is, each time, subject to the inconveniences caused by the withdrawal of blood samples. The devices disclosed in the above-mentioned U.S. patent speifications require removal of the surface layer of the skin where they are to be applied, which, again, leads to considerable inconveniences to the patient.

The present invention provides a method which permits continuous, or, if desired, intermittent monitoring of a patient's in vivo plasma pH over a period, without the necessity of using electrodes which require removal of skin layers, and without the necessity of repeated withdrawals of blood samples.

The method of the invention for continuous or intermittent monitoring of a patient's in vivo plasma pH comprises establishing the patient's acid base status (in the following called the initial acid base status) with performance of at least one in vitro determination on a blood sample withdrawn from the patient, and thereafter determining the patient's in vivo plasma pH on the basis of the thus established initial acid base status and on the basis of continuously or intermittently registered results of a non-invasive measurement of the patient's actual blood $Pco_2$.

The method of the invention permits the continuous or intermittent monitoring of a patient's in vivo plasma pH with sufficient exactitude over a period, in practice a period of several hours, without the necessity of performing determinations on more than one blood sample from the patient. In the process of the invention, one utilizes at least one in vitro determination on the blood sample withdrawn from the patient for establishing the patient's initial acid base status. The remaining pH determinations in the period thereafter are performed on the basis of the results of the non-invasive measurement of the patient's actual blood $Pco_2$, as the invention, such as described in greater detail below, utilizes the fact that once the patient's acid base status has been established, the pH may, for a considerable period thereafter, be expressed on the basis of the blood $Pco_2$.

The very measurement of the patient's blood $Pco_2$ in a non-invasive manner does not constitute any part of the present invention. Apparatus for non-invasive, especially transcutaneous, determination of blood $Pco_2$, in other words, the partial pressure of $CO_2$ in the blood, has recently been developed and is currently being developed. Suitable sensors for relatively inconvenience-free transcutaneous $Pco_2$ determinations are $Pco_2$ electrodes which are heated to above skin temperature and which, when applied against the skin, heat the skin in the measuring area, vide for example Anesthesiology, Vol. 21, No. 6, November-December 1960, pages 717–726, especially 722, and Anaesthesist, 22, 379–380 (1975), Journal of Applied Physiology, 41, No. 3, September 1976, 442–447, and The Lancet, May 7, 1977, 982–983. However, also other non-invasive methods permitting the determination of a patient's blood $Pco_2$ are known, vide for example U.S. Pat. No. 4,005,700 which discloses the use of mass spectrometry on gas in equilibrium with heated skin.

Several workers have investigated the acid base conditions of blood, especially human blood, and comprehensive collections of parameter sets have been prepared, for example in the form of tables, algorithms, computer programs, nomograms and curve nomograms. By means of these one can, from a given set of parameters for a blood sample, for example pH, $Pco_2$ and hemoglobin concentration, determine other parameter values, including for example the bicarbonate concentration in plasma, actual base excess of the blood and, when the oxygen saturation (defined below) is known, also base excess of completely oxygenated blood, the blood's buffer base and standard bicarbonate.

A detailed review of the acid base status of the blood is given by Ole Siggaard-Andersen in "The Acid-Base Status of the Blood", 4th edition, Munksgaard, Copenhagen, 1974, issued simultaneously in the United States by William & Wilkins Company, Baltimore. In this book, the author states various suitable parameter relations as equations, nomograms and curve nomograms, but also mentions other parameter relations stated by other workers.

Of special interest in this connection is the so-called acid base status which in principle is determined when at least two acid base quantities for the patient's extracellular liquid are determined, typically the pH and $Pco_2$ of the arterial blood. In this connection the expression "the patient's acid base status" indicates a set of connected values for pH and $Pco_2$ in the patient's arterial blood or, with sufficient approximation, arterialized capillary blood, for example from the ear lobe. In accordance with this, the patient's acid base status may be determined by measuring of pH and $P_{CO_2}$ on an arterial blood sample or capillary blood sample from the patient, when the said blood sample has been withdrawn and transferred to the measuring apparatus under anaerobic conditions.

It has been empirically ascertained and theoretically supported that a patient's acid base status, expressed as connected values of pH and $P_{CO_2}$, will always change according to a certain relation, as long as the patient has not had any substantial chemical exchange with the surroundings other than by respiration, except in the rare (and easily ascertainable) cases where the patient undergoes abnormal metabolic disturbances as for instance in case of diabetes. This is, explained in a simplified manner, due to the fact that changes in $P_{CO_2}$ (as by respiration) changes pH without influencing the concentration of non-carbonic acid or base. In other words, for a given concentration of non-carbonic acid or base, a certain pH will correspond to a given $P_{CO_2}$. Considerable changes in the relation between $P_{CO_2}$ and pH will arise when the patient has chemical exchange with the surroundings in other ways than by respiration, for example by blood transfusion. When, however, such considerable changes do not occur, the relation between $P_{CO_2}$ and pH will be established over a period of several hours, in practice up to 3-10 hours, and this fact is utilized in the present invention. Minor variations in the relation between $P_{CO_2}$ and pH may arise due to changes in the oxygen saturation (defined below). In practice, these variations due to the changes in the oxygen saturation are so small that they can be ignored in most cases. But the method of the invention also permits taking them into consideration.

On the basis of the above-mentioned explanation it is understood that when a patient's acid base status has been established, an unambiguous relation between pH and $P_{CO_2}$ for a considerable period will exist in practice. By using the parameter relation between $P_{CO_2}$ and pH, the registered results of the $P_{CO_2}$ measurement may be expressed as pH values.

The relation between blood parameters are not unanimously indicated by all workers, and a quite "absolute" parameter relation which is incontrovertibly true for all patients, can hardly be given. The various proposed parameter relations are therefore to be considered as approximations which have shown their applicability and sufficient exactitude in practice. Values fixed by definition form part of the parameter relations and their calculations for certain parameters in certain relations, and these values may also vary from worker to worker. In principle, any parameter relation which has been found to be clinically applicable may be used for the purpose of the present invention for transformation of the transcutaneously measured $P_{CO_2}$ to pH, whether this parameter relation is expressed as equations, nomograms, curve nomograms or computer programs. In connection with the following explanation of the invention, however, reference is made to the parameter relations which are stated by Ole Siggaard-Andersen in the above work and which enjoy general acceptance.

According to the present invention, the patient's initial acid base status is established with performance of at least one in vitro determination on a blood sample withdrawn from the patient. As mentioned above, a determination of pH and $P_{CO_2}$ in an anaerobically withdrawn arterial or capillary blood sample from the patient will establish the patient's acid base status.

The determination of pH and $P_{CO_2}$ on an anaerobically transferred arterial or capillary blood sample withdrawn from the patient is performed by means of a pH transducer and a $P_{CO_2}$ transducer, respectively. They may be electrodes of a type known per se, which are calibrated in advance so that they, when measuring, indicate true values for pH and $P_{CO_2}$. For establishing the patient's initial acid base status it is sufficient to perform one of these in vitro determinations on a anaerobically transfered arterial blood sample withdrawn from the patient, in practice a determination of pH. The other value, in practice $P_{CO_2}$, may, instead of being determined on the blood sample, be the value registered from a non-invasive measurement performed on the patient with a calibrated transducer simultaneously with the withdrawal of the blood sample.

According to an aspect of the present invention, a $P_{CO_2}$ measurement is performed in vitro on the anaerobically transferred arterial or capillary blood sample, even when an in vivo, that is, non-invasive, measurement of $P_{CO_2}$ has been performed simultaneously with the withdrawal of the blood sample. For the in vitro $P_{CO_2}$ measurement, a calibrated $P_{CO_2}$ transducer, for example a calibrated $P_{CO_2}$ measuring electrode, is used. Thus the difference between the in vitro measured and the in vivo measured $P_{CO_2}$ may be used directly for calibration of the in vivo $P_{CO_2}$ measuring device in the condition in which it is positioned for the purpose of the measurement, the reading or registration of the in vivo $P_{CO_2}$ measuring instrument being corrected on the basis of the difference.

However, the method of the invention does not even necessitate measurements on an anaerobically transferred arterial or capillary blood sample from the patient. The initial acid-base-status may also be established on the basis of a non-anaerobically transferred blood sample, whether it is an arterial, a capillary or a vein blood sample. In this case, however, it is necessary to perform measurement of sufficient blood parameters for determining the pH, $P_{CO_2}$ and hemoglobin content of the sample (in practice this usually means determination of the pH and $P_{CO_2}$ of the sample and of a further blood parameter which is either the hemoglobin content or another blood parameter being a function of the hemoglobin content (or the hemoglobin content may as an approximation be fixed as 9.3 mmol/liter) and for the establishing, also the result of a measurement of the patient's actual blood pH and $P_{CO_2}$ performed simultaneously with the withdrawal of the blood sample is required, which in practice may be a non-invasive $P_{CO_2}$ measurement with a calibrated $P_{CO_2}$ measurement unit. With this set of parameters and using known parameter relations for the in vitro acid base status of the blood, for example such as stated by Ole Siggaard-Andersen in the above-mentioned work, it is possible to determine the patient's acid base status at the moment of the withdrawal of the blood sample.

This establishing of the patient's initial acid base status may in principle be performed by determining, on the basis of the hemoglobin determination (or the hemoglobin fixed, as an approximation, at 9.3 mmol/liter) and the connected values of pH and $P_{CO_2}$ measured on the blood sample, the function along which connected values of pH and $P_{CO_2}$ vary for the blood sample in question, and subsequently inserting the $P_{CO_2}$ measured at the moment of the withdrawal of the blood sample and determining the corresponding pH. The calculations in question may be performed by using the above-mentioned parameter relations in the form of equations, computer programs, nomograms or curve nomograms. This establishing of the patient's acid base status will be sufficiently exact in most cases.

A further increase of the exactitude when determining the patient's initial acid base status on the basis of a non-anaerobically withdrawn blood sample is obtained by correcting for possible differences between the oxygen saturation in the blood sample at the time of the in vitro determination and the oxygen saturation at the time of withdrawal of the sample.

The oxygen saturation is defined as the ratio between hemoglobin saturated with oxygen and the sum of hemoglobin saturated with oxygen plus hemoglobin without oxygen and may, for example, be determined photometrically by means of a so-called oxymeter or may be calculated on the basis of a determination of $Po_2$. When it is desired to correct for possible differences in oxygen saturation between the patient's blood at the time of the withdrawal of the sample and the blood sample in the condition in which it is subjected to measurement in vitro, it is necessary to use the result of a $Po_2$ measurement or a saturation measurement, preferably performed on the patient in a non-invasive way, at the time of the withdrawal of the blood sample, together with the result of a corresponding determination of the oxygen saturation, that is, either by a $Po_2$ measurement or by means of photometric measuring apparatus, performed simultaneously with the pH and $Pco_2$ determination on the blood sample. In principle, the correction of the patient's acid base status to compensate for differences between the oxygen saturation of a non-anaerobically transferred blood sample and the oxygen saturation at the transfer moment may be performed by displacing, on the basis of the difference in the oxygen saturation, the curve for connected values of pH and $Pco_2$, inserting, on the displaced curve, the $Pco_2$ measured at the sample withdrawal moment, and reading the corresponding pH. As mentioned, the correction for the saturation will in practice be relatively small as it appears from the examples.

Irrespective of how the patient's initial acid base status is established, it may be desirable, for the sake of accuracy, continuously to take into consideration possible changes in the oxygen saturation. This, of course, necessitates that the initial oxygen saturation be established which, for the anaerobically transferred arterial or capillary blood sample, is done simply by a photometric measurement or a $Po_2$ measurement on the blood sample.

When the patient's initial acid base status has been established in one of the above-described ways, the further monitoring of the pH according to the invention takes place on the basis of the thus established initial acid base status and on the basis of continuously or intermittently registered results of non-invasive measurement of the patient's actual blood $Pco_2$. Also in this connection, accepted parameter relations are used, the condition being that the function used for connected values of the patient's extracellular pH and $Pco_2$, the so-called "in vivo $CO_2$ equilibration line" or "Base Excess line", includes, at unchanged oxygen saturation, the initial acid base status as a function value. In principle, this function is, in suitable representations, a straight line. As a point on this line has been established as the patient's initial acid base status in the above-described way, only the establishing of the slope is necessary for the further application. This may be done by using empiric/definition values, for example a definition value of 3.7 mmol/liter for the hemoglobin concentration in vivo. The below examples show various methods for determining the patient's in vivo base excess line.

In the further monitoring of the patient, the pH is determined each time on the basis of the continuously or intermittently registered results of the non-invasive blood $Pco_2$ measurement by means of the thus established Base Excess line. All the time, instead of the registered $Pco_2$ in question, the corresponding pH is read. The expression "is read" is not to be taken literally; in practice the conversion units will usually, instead of curves and curve sensors, include computers in which the parameter relations in question are programmed in advance. To obtain the highest exactitude, also changes in the oxygen saturation may be monitored by means of a non-invasion transducer, for example a non-invasive $Po_2$ electrode or an ear oxymeter; when the oxygen saturation changes, the Base Excess line is displaced correspondingly.

The present invention also concerns an apparatus for use in the method of the invention. This apparatus comprises an input for signals representing the result of a non-invasive $Pco_2$ measurement and an input for introducing at least one blood parameter determined by in vitro measuring on a blood sample, and further comprises a pH registration unit which is connected to the first mentioned input through a conversion unit, the conversion unit being adapted to perform the conversion of the received $Pco_2$ signals into pH units as a function of a parameter set introduced into the conversion unit, the parameter set representing an initial acid base status and comprising at least one blood parameter determined by in vitro measurement and introduced through the last-mentioned input.

The transmission unit of such an apparatus will in practice preferably comprise a microcomputer which has a sufficient memory for the purpose, and into which the parameter relations, expressed as for instance equations (vide, e.g., the examples), have been introduced, the microcomputer establishing, at given inserted parameter set representing an initial acid base status, the slope of the Base Excess line through the point corresponding to this acid base status, and thereafter converting measured $Pco_2$ values and expressing them as pH. In the special case where the oxygen saturation or oxygen saturation differences are ignored in these conversions, the conversion unit and its programming may be particularly simple, as, in this case, all Base Excess lines converge, with sufficient approximation, to a single point (vide Example 4.d).

In accordance with what has been explained above, the parameter set which represents an initial acid base status may be established in different ways, but each time the parameter set comprises at least one blood parameter which is either the pH determined on a blood sample withdrawn from the patient or a blood parameter of which is a function of this pH as described above, the parameter set which represents an initial acid base status may completely be determined in vitro on an anaerobely withdrawn blood sample, and the whole parameter set which represents this acid base status will thus be introduced into the conversion unit through the input adapted thereto. As it appears from the above disclosed, it is also possible to establish the parameter set representing the initial acid base status, by using both one or more in vitro measured blood parameters and a non-invasive measurement of usually $Pco_2$ (and possibly $Po_2$ or the oxygen saturation) performed simultaneously with the blood sample withdrawal in question. In this case, the establishing of the initial acid base status is performed by the conversion unit on the basis of partly the "in vitro input" and partly the "in vivo input".

An apparatus according to the present invention is suitably equipped with a unit, in connection with the in vitro input, for introduction of the blood parameter(s) determined in vitro for establishing the initial acid base status. This unit may, for example, be a pH measuring equipment of the conventional kind (for introduction of in vitro pH), a blood gas equipment (from which in vitro pH and, according to the construction and design of the blood gas equipment, other in vitro blood parameters which might be necessary for establishing the initial acid base status in question, may be introduced including, for example, in vitro $Pco_2$, in vitro hemoglobin content and in vitro $Po_2$). The unit may also simply be a keyboard, which in addition to pH may be adapted to introduce any desired in vitro blood parameter or blood parameter set, including a complete initial acid base status determined with separate equipment. The apparatus may also be equipped with both a measuring unit, for example a pH measuring equipment or a blood gas equipment, and a keyboard, the keyboard then being useful for introducing parameters which cannot be measured on the measuring unit or which in the specific situation will not be measured on the measuring unit.

In a special embodiment the apparatus comprises, besides the pH registration unit, a $Pco_2$ registration unit which is in connection with the input of signals representing the result of a non-invasive $Pco_2$ measurement, so that the invasively measured $Pco_2$ values may be read on the apparatus. For use in the cases where it is desired to take the oxygen saturation into consideration, it is suitable that the apparatus comprises an input for signals representing the result of a non-invasive $Po_2$ measurement or oxygen saturation measurement, and that this input communicates with the conversion unit. This permits the result of the non-invasive $Po_2$ measurement or oxygen saturation measurement to be included in the calculation performed by the conversion unit, such as described above. When the apparatus comprises an input for signals from an in vivo $Po_2$ measurement, it may be desirable also to include a $Po_2$ registration unit in the apparatus, connected with the said input, so that one can read information about the measured $Po_2$ value on the apparatus, or have the apparatus deliver this as read-out.

According to a preferred embodiment of the apparatus, it comprises a synchronizing unit which, when activated, stores, in the conversion unit, the non-invasive $Pco_2$ value measured at the activating time and—if the apparatus also comprises an input for a non-invasive $Po_2$ electrode or an ear okimeter, and it is desired, for the measurement in question, to take into consideration the oxygen saturation—also the non-invasively measured $Po_2$ value or oxygen saturation value registered at the activating time. When this synchronizing unit is activated at the time where a blood sample is withdrawn from the patient, it is secured that the non-invasively measured initial $Pco_2$ and optional $Po_2$ or saturation value stored in the conversion unit is/are the value(s) which exactly applied at the time of the withdrawal of the blood sample, and hence is/are the value(s) to be related to the in vitro measurement. This is relevant for all the cases where the in vitro measurement is to be combined with an in vivo measurement performed simultaneously with the blood sample withdrawal, in other words for example when the in vitro measurement is performed on a non-anaerobically transferred blood sample, or where the in vitro measurement on an anaerobically transferred blood sample does not comprise the complete parameter set representing acid base status. Another case in which a synchronization between the blood sample withdrawal and a non-invasive measurement is desired is when it is desired to take the oxygen saturation into consideration, and the initial oxygen saturation is determined on the basis of a non-invasive $Po_2$ measurement or oxygen saturation measurement. A further utilization of synchronization between the blood sample withdrawal and a non-invasive measurement is for calibration of the non-invasive transducer. For example, the pH measuring instrument signal from an initial measurement on an anaerobically transferred arterial or capillary blood sample together with the simultaneous signal from the non-invasive $Pco_2$ transducer may simply serve for automatic calibration, by the conversion unit, of the read-out of the non-invasive $Pco_2$ transducer, expressed as pH. (Another calibration possibility of this kind is that an initially determined pH pertaining to the acid base status of the patient is, by means of the keyboard, read into or transferred into the pH registration equipment of the apparatus). The synchronization unit in its simplest embodiment may be a button positioned on the apparatus and operated manually at the time of the blood sample withdrawal, or it may comprise an input which through an electric cord or cable is in communication with a button positioned at the blood sample withdrawal station for manual operation, or with a transducer connected to the blood sample withdrawal apparatus, said transducer being automatically activated when the blood sample withdrawal is performed.

The invention is now described in greater detail with reference to the drawing, in which

FIGS. 1–6 are discussed in greater detail in connection with the examples.

Figure 7:
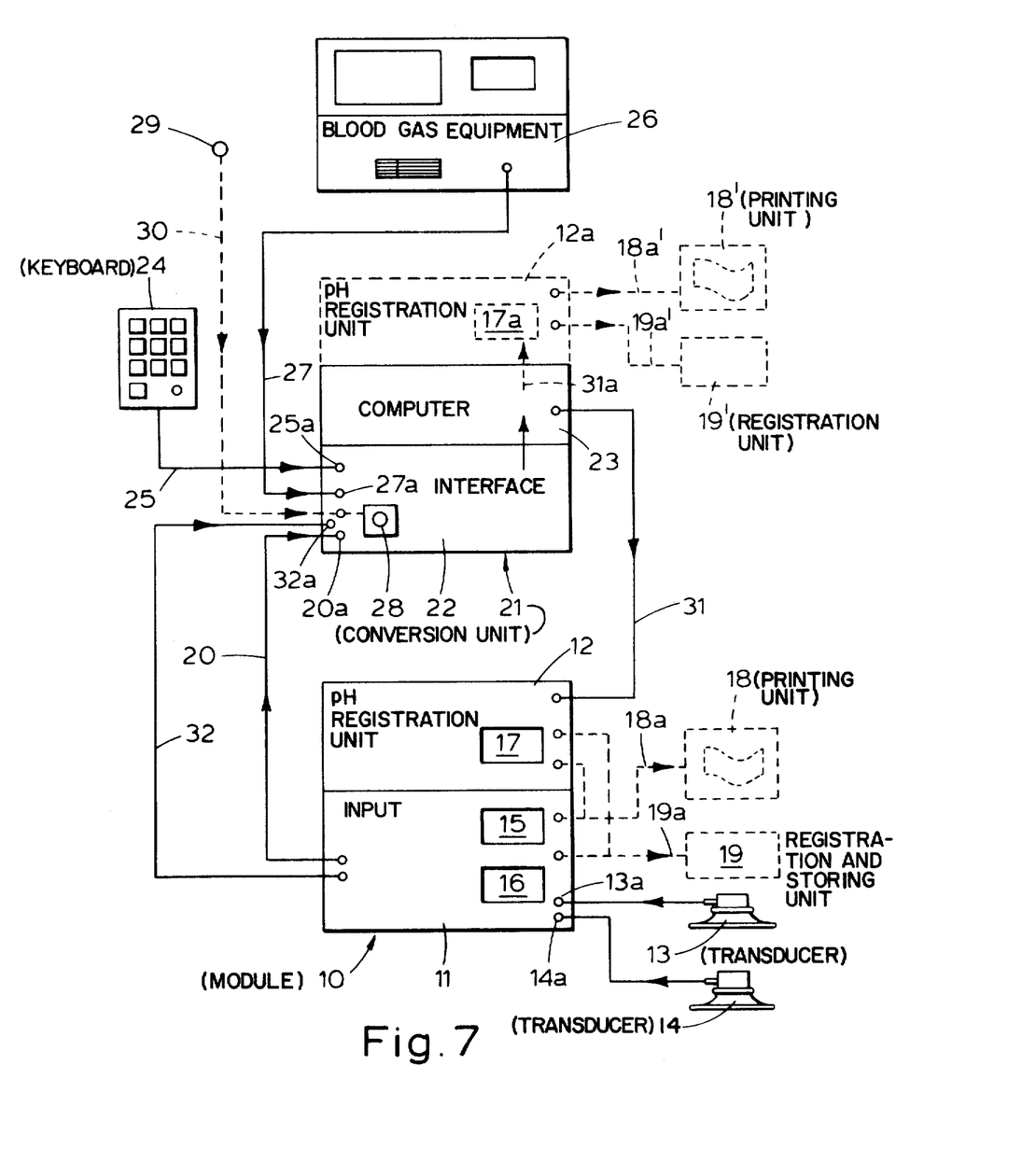
FIG. 7 is a schematic representation of an apparatus according to the invention.

Reference is made to FIG. 7 which is a schematic representation of an embodiment of an apparatus of the invention. A module 10 comprises an input part 11 which, in the embodiment shown, is equipped with a $Pco_2$ registration unit being for example a digital display 15 which, through an amplifier (not shown) communicates with an input 13a for signals from a non-invasive $Pco_2$ transducer 13 (shown as a heated $Pco_2$ electrode), and which shows the non-invasively measured $Pco_2$ value designated "$T_c$-$Pco_2$". The input part 11 may additionally comprise for example a $Po_2$ registration unit in the form of for example a digital display 16, which in a corresponding way, through an amplifier, communicates with an input 14a for signals from a non-invasive $Po_2$ transducer 14 (shown as a heated $Po_2$ electrode) and which shows the non-invasively measured $Po_2$ value, designated "$T_c$-$Po_2$". In the embodiment shown, the module 10 further comprises a pH registration unit 12 with for example a digital display 17 showing the calculated in vivo pH value, designated "in vivo pH". As an alternative or supplement to the digital displays 15, 16 and 17, the module may comprise a printing unit 18 which through a line 18a communicates with the respective registration units, or the module may comprise any other registration unit, for example a central registration and storing unit 19 of any suitable kind, which may for example serve several apparatuses of the kind described and which in the embodiment shown communicates with the registration units through a line 19a. The input part 11 supplies, via a connection 20, signals, suitably in digitalized form, representing the non-invasively measured $P_{CO_2}$ and (if a non-invasive $P_{O_2}$ measurement is performed) via a connection 32 signals, also suitably in digitalized form, representing the non-invasively measured $P_{O_2}$, to an interface part 22 of a conversion unit 21. The interface part 22 is equipped with an input 25a and/or 27a for introducing in vitro measured parameters, the input 25a being connected, via a connection 25, with a manually operated keyboard 24, and the input 27a being connected, via a connection 27, with a pH meter or blood gas equipment 26. The interface part is also equipped with a synchronizing unit which may be a manually operated button 28 or a suitable transducer or remote control button 29 which, through a connection 30, is connected to the interface part. The interface part is connected to a computer part 23 of the conversion unit 21, which, through a connection 31 is connected to the in vivo pH registration unit 12.

In practice, the design of the single modules and the extend to which they are built together will be dictated by the particular facilities and conditions prevailing at the location of use. One suitable apparatus for many of the relevant uses will comprise the module 10 built together with the conversion unit 21 and equipped with the keyboard 24. Such an apparatus may, according to what is needed, comprise solely the $P_{CO_2}$ transducer 13 as transcutaneous measuring unit, or it may comprise both the $P_{CO_2}$ transducer 13 and the $P_{O_2}$ transducer 14. Alternatively, the apparatus consisting of the modules 10 and 21 may be built together with a blood gas measuring equipment or a pH measuring equipment 26, or it may suitably simply be equipped with the input 27a for on line transfer of measuring results from a pH measuring equipment or blood gas measuring equipment. In another embodiment, the conversion unit 21 may be built together with an in vivo pH registration unit 12a with, for example, a digital display 17a and/or a printing unit 18' or another registration unit 19', which through connections 18'a or 19', respectively, is connected with the registration unit, the computer part 23 in this case communicating with the pH registration unit 50 through a connection 31a. This way of building together the units may be practical for larger plants in which a central conversion and registration unit calculating in vivo pH serves a number of individual non-invasive $P_{CO_2}$ registration units, each comprising non-invasive transducer 13 and input part 11 with amplifier, etc., which in this case is not itself equipped with any display. An apparatus consisting of the conversion unit 21 and the pH registration unit 12a may also be a practical supplement for existing non-invasive $P_{CO_2}$ measuring equipment.

The invention is further illustrated in the below examples.

Examples 1 illustrates how a curve nomogram is used, especially in connection with the establishment of a patient's initial acid base status from in vitro measurements performed on a non-anaerobically transferred blood sample.

Example 2 shows the same type of determination, but in this case performed by calculation.

Example 3 illustrates various determinations of the patient's initial acid base status.

Example 4 illustrates the use of the patient's acid base status for establishing the in vivo Base Excess line using partly nomogram and partly calculation, and the use of the in vivo Base Excess line for determining the in vivo plasma pH value utilizing results of non-invasive determinations of the patient's actual blood $P_{CO_2}$.

In connection with the examples the following definitions are used:

Actual Base Excess (ABE): The difference in concentration of strong base in the blood between on the one hand the actual blood sample and on the other hand the same blood titrated with a strong base or acid to pH 7.4, $P_{CO_2}$ 40 mm Hg and a temperature of 37° C. The titration is performed at constant oxygen saturation which is the same as the one in the arterial blood of the person.

Base Excess (BE): Same definition as ABE, but with the titration performed at complete oxygen saturation.

In Vivo Base Excess (SBE): Same as ABE, but with a fixed standard hemoglobin concentration of 3.7 millimol/liter.

Saturation (Sat): $Sat = HbO_2/(HbO_2 + Hb)$ in which $HbO_2$ is the concentration of hemoglobin saturated with oxygen, and Hb is the concentration of hemoglobin without oxygen.

Buffer Base (BB): Indicates the concentration of buffer anions in the blood when all hemoglobin is present as $HbO_2$.

Normal Buffer Base (NBB): Is the buffer base value of blood with pH 7.4, $P_{CO_2}$ 40 mm Hg and temperature 37° C.

$$NBB = 41.7 + 0.68 \times Hb \text{ mmol/liter} \quad (1)$$

Actual Buffer Base (ABB): Buffer Base value at actual oxygen saturation (is only used as a calculating quantity.

$$ABB = BB + 0.31 \times Hb (1 - Sat) \text{ mmol/liter} \quad (2)$$

Besides, the following relations exist between the above-mentioned quantities:

$$BE + BB - NBB = BB - (41.7 + 0.68 \times Hb) \text{ mmol/liter} \quad (3)$$

$$ABE = BE + 0.31 \times Hg (1 - Sat) \text{ mmol/liter} \quad (4)$$

$$ABB - ABE = NBB \text{ mmol/liter} \quad (5)$$

EXAMPLE 1

By means of a blood gas equipment (Radiometer ABL 2), the following values have been measured on a non-anaerobically transferred blood sample:

pH = 7.2

$P_{CO_2}$ = 30 mm Hg $P_{O_2}$ = 200 mm Hg ~ Sat = 1

Hb = 10 millimol/liter.

Simultaneously with the withdrawal of the blood sample, the following values were measured transcutaneously on the patient:

$P_{CO_2} = 50$ mm Hg $P_{O_2} = 37.3$ mm Hg $\sim$ Sat $= 0.5$

Figure 1:
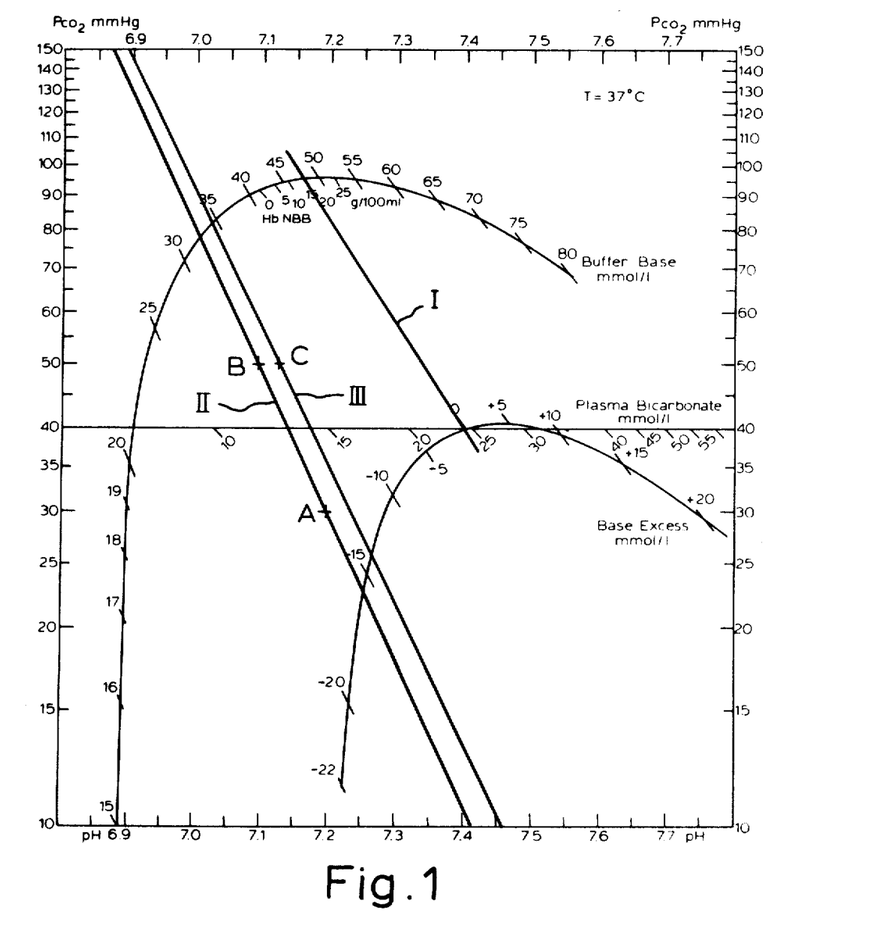
FIGS. 1–6 show curve nomograms illustrating the determinations performed in the below examples.

On the basis of these parameters, the initial acid base status of the patient is established with maximum exactitude (that is, taking into consideration the oxygen saturation) in the following way:

Firstly, a point (A) is plotted in the curve nomogram in FIG. 1, corresponding to the pH and $P_{CO_2}$ of the blood sample. Utilizing the Hb value, the line I from BE=0 to BB=41.7+0.68×10=48.5 (confer equation (1)) is drawn. This line is thereafter displaced the same number of units along the BB and BE curves, until it passes through point (A) (line II). Equation (5) is now fulfilled.

Thereafter, the point (B) is plotted on line II corresponding to the transcutaneously measured $P_{CO_2}$. The pH in this point is 7.098. Point B represents the patient's initial acid base status, when the saturation difference between the patient and the non-anaerobically transferred blood sample is not taken into consideration. Correction for this saturation difference to obtain the more exact value is performed by displacing the Base Excess line (II) by the quantity $0.31 \times 10(1-0.5) = 1.55$ along both the BE and the BB curves (equation (2) and (4)). This results in line III which passes through ABE=−14.1 and ABB=34.4, while line II passed through ABE=BE=−15.7 and ABB=BB=32.8. On line III the transcutaneously measured $P_{CO_2}$ (50 mm Hg) is not plotted, and pH in the resulting point (C) is 7.126. Hence, the patient's initial acid base status was: $P_{CO_2}$ 50 mm Hg, pH 7.126.

EXAMPLE 2

From a blood sample withdrawn from a patient and transferred in a non-anaerobical manner, the following values have been measured by means of a blood gas equipment:

pH = 7.2

$P_{CO_2} = 30$ mm Hg $P_{O_2} = 200$ mm Hg $\sim$ Sat $= 1$

Hb = 10 millimol/liter.

Simultaneously with the withdrawal of the blood sample, the following values have been measured transcutaneously:

$P_{CO_2} = 50$ mm Hg $P_{O_2} = 37.3$ mm Hg $\sim$ Sat $= 0.5$.

Now follows an explanation of how the calculation of the patient's initial acid base status is performed on this basis. The calculation may be performed by means of a computer. The explanation is illustrated by the curve nomogram in FIG. 2. The coordinates of the BE and BB curves are known (for example from p. 54 in the work by Ole Siggaard-Andersen previously mentioned), and ABE may be calculated with good approximation.

Figure 2:
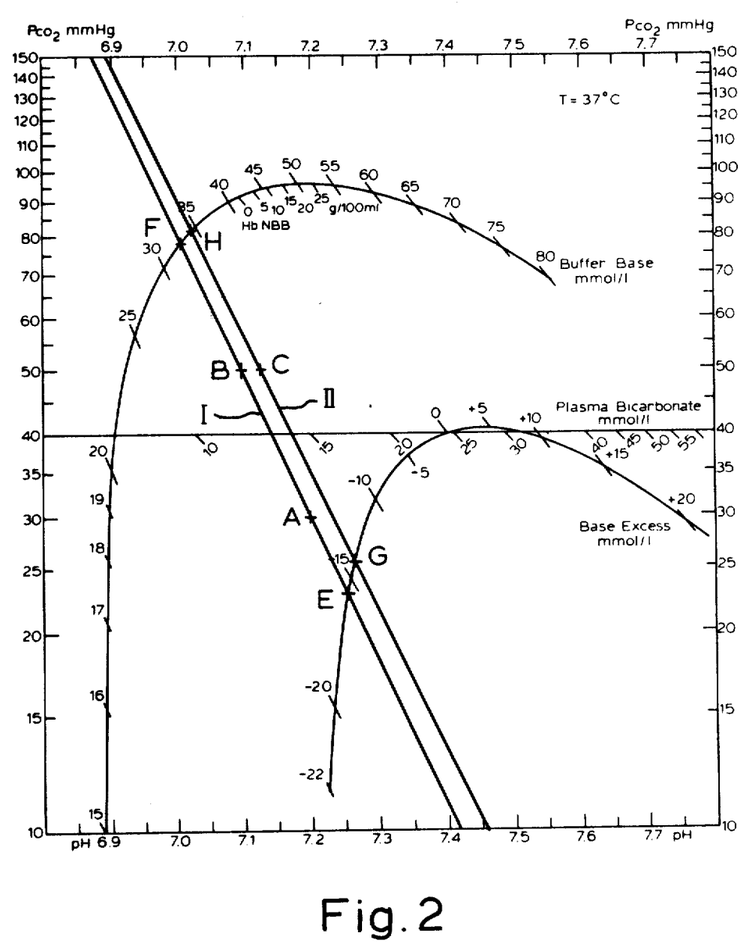

The point A in FIG. 2 represents the parameter set measured on the blood sample: pH=7.2 and $P_{CO_2}=30$ mm Hg. Calculation is performed:

$$ABE = Z(1 - 0.000383 \times Hb(Z+25.11) - 2.755 \times Hb) \quad (6)$$

wherein $$Z = (1 - 0.0230 \times Hb)(HCO_3 - 24.5 + (8 + 2.25 \times Hb)(-pH - 7.4)) \quad (7)$$

and $HCO_3$ is the bicarbonate concentration in plasma which may be found by:

$$HCO_3 = 0.0306 \times P_{CO_2} \times 10^{\frac{pH - 6.161}{0.9524}} \quad (8)$$

ABE is calculated to $-15.88$ millimol/liter (point E). ABB=NBB+ABE=41.7+0.68×Hb+ABE=32.67 millimol/liter (point F).

The co-ordinates of points E and F may be found by linear interpolation:

$$pH_E = (pH_{-16} - pH_{-15}) \times 0.83 + pH_{-15} \quad (9)$$

$$\log P_{CO_2 E} = (\log P_{CO_2 -16} - \log P_{CO_2 -15}) \times 0.83 + \log P_{CO_2 -15} \quad (10)$$

$pH_E = 7.253$ $P_{CO_2 E} = 22.58$ mm Hg $$pH_F = (pH_{33} - pH_{32}) \times 0.67 + pH_{32} \quad (9')$$

$$\log P_{CO_2 F} = (\log P_{CO_2\, 33} - \log P_{CO_2\, 32}) \times 0.67 + \log P_{CO_2\, 32} \quad (10')$$

$pH_F = 7.004$ $P_{CO_2 F} = 78.23$ mm Hg

From the coordinates for E and F the Base Excess line I may be calculated:

$$\log P_{CO_2} = \frac{\log P_{CO_2\, F} - \log P_{CO_2\, E}}{(pH_F - pH_E)} (pH - pH_E) + \log P_{CO_2\, E} \quad (11)$$

$\log P_{CO_2} = -2.167 \times pH + 17.072$

When the $P_{CO_2}$ of 50 mm Hg measured simultaneously with the withdrawal of the blood sample is inserted, pH 7.094 results (point B).

When the fact that the patient's saturation was 0.5 at the sample withdrawing time is taken into consideration, the Base Excess line will be displaced with the quantity $0.31 \times 10(1-0.5) = 1.55$ along both the BE and the BB curves (equations 2 and 4) to ABE=−14.28 (G) and ABB=34.25 (H).

The coordinates of points G and H may be calculated according to the equations 9, 10 and 9', 10' with the new values introduced $pH_G = 7.264$ $P_{CO_2 G} = 25.21$ $pH_H = 7.020$ $P_{CO_2 H} = 81.57$ The Base Excess line may thereafter be calculated according to equation 11:

$$\log P_{CO_2} = -2.090 \times pH + 16.583.$$

When the trancutaneously measured $P_{CO_2}$ of 50 mm Hg is inserted, the corresponding pH is calculated to 7.122 (point C). The patient's initial acid base status was then pH 7.122 and $P_{CO_2}$ 50 mm Hg.

EXAMPLE 3

(a) Utilizing an apparatus as illustrated in FIG. 7, a patient is monitored with a transcutaneous $P_{O_2}$ electrode (14) and a transcutaneous $P_{CO_2}$ electrode (13). A blood sample is withdrawn from the patient (for example vein blood), and the transcutaneously measured $P_{O_2}$ and $P_{CO_2}$ values are transferred, by activating the button 28, to the computer (23) the same moment the sample is withdrawn. The values are:

$$P_{O_2} = 37.3 \text{ mm Hg}$$

$$P_{CO_2} = 50.0 \text{ mm Hg}$$

The blood sample is kept at room temperature and in contact with atmospheric air. Thereafter, the blood sample is analyzed on blood gas equipment (26), and the same values as are stated in Example 2 are measured, in other words corresponding to point A in FIG. 2. These values are transferred via the connection 27 and the interface part 22 to the computer 23. The patient's actual pH is calculated when the values in A have been accepted, like in Example 2 as a first approximation to 7.094 (point B).

At this pH and the transcutaneously measured $P_{O_2}$, the saturation is calculated using the equations:

$$Sat = \frac{Z^{2.6}}{(26.6^{2.6} + Z^{2.6})} \quad (12)$$

wherein $$Z = P_{O_2} \times 10^{(-0.48(7.4 - pH))},$$

$$Sat = 0.5. \quad (13)$$

Thereafter, the in vitro Base Excess line II is calculated for Sat=0.5 like in Example 2, and by means of this line and the transcutaneously measured $P_{CO_2}$ of 50, the patient's actual pH is calculated to 7.122. Hereafter, the patient's initial acid base status is established like in Example 2, and until a change of the transcutaneously measured values is registered, the three displays will show pH 7.122, $P_{CO_2}$ 50.0 mm Hg and $P_{O_2}$ 37.3 mm Hg, respectively. The patient's so-called "in vivo acid base status" shows the same values as in Example 2 with the exception of the III which is fixed per definition to 3.7 millimol/liter in vivo. This value is of importance for the establishing of the patient's in vivo Base Excess line, confer Example 4.

(b) The patient's in vivo acid base status may also be determined directly on a blood sample (arterial blood) withdrawn anaerobically and thereafter analyzed on a separate blood gas equipment:

$$pH = 7.122$$

$$P_{CO_2} = 50.0 \text{ mm Hg}$$

$$P_{O_2} = 37.5 \text{ mm Hg} - Sat = 0.5.$$

By means of the keyboard 24 the pH and the $P_{CO_2}$ value and, if the oxygen saturation is to be taken into consideration, the $P_{O_2}$, are keyed into the conversion unit 21 via the connection 25.

To the patient's in vivo acid base status also pertain: Hb=3.7 equivalent Hb in vivo, fixed per definition.

(c) Using an apparatus as illustrated in FIG. 7, a patient is monitored with a transcutaneous $P_{O_2}$ electrode (14) and a transcutaneous $P_{CO_2}$ electrode (13). A blood sample (arterial blood) is withdrawn anaerobically from the patient. Simultaneously with the blood sample withdrawal, the transcutaneously measured $P_{O_2}$ and $P_{CO_2}$ values are transferred to the computer 23 by activating the button 28.

$$P_{O_2} = 37.3 \text{ mm Hg}$$

$$P_{CO_2} = 50.0 \text{ mm Hg}$$

The pH in the blood sample is measured on a separate pH measuring equipment, and the result is keyed in via the keyboard 24.

$pH_{actual} = 7.122$. When this value has been accepted, it is transferred to the computer 23.

The patient's in vivo acid base status is now established:

$$pH = 7.122$$

$$P_{CO_2} = 50.0 \text{ mm Hg}$$

$$P_{O_2} = 37.2 \text{ mm Hg}$$

Hb=3.7 millimol/liter, fixed per definition.

(d) Using the apparatus shown in FIG. 7, a patient is monitored with a transcutaneous $P_{O_2}$ electrode (14) and 1 transcutaneous $P_{CO_2}$ electrode (13). A blood sample (arterial blood) is withdrawn anaerobically from the patient. Simultaneously with the withdrawal of the blood sample, the transcutaneously measured $P_{O_2}$ and $P_{CO_2}$ are transferred to the computer 23 by activating the button 28.

$$P_{O_2} = 25.0 \text{ mm Hg}$$

$$P_{CO_2} = 55.0 \text{ mm Hg}.$$

The blood sample is analyzed on the blood gas equipment 26. The following values are found:

$$pH = 7.122$$

$$P_{CO_2} = 50.0 \text{ mm Hg}$$

$$P_{O_2} = 37.3 \text{ mm Hg},$$

which by means of the on-line connection 27 is transferred to the computer 23.

Using the transcutaneously measured values stored in the computer and the values measured with the blood gas equipment, the transcutaneous electrodes are calibrated, transcutaneous $P_{O_2} = f(P_{O_2} \text{ arterial})$ and transcutaneous $P_{CO_2} = f(P_{CO_2} \text{ arterial})$.

The patient's in vivo acid base status is established:

$$pH = 7.122$$

$Pco = 50.0$ mm Hg $Po_2 = 37.3$ mm Hg ~ Sat = 0.5

Hb = 3.7 millimol/liter, fixed per definition.

In all the cases mentioned in Example 3, the in vitro $Po_2$ and in vivo $Po_2$ measurements may be replaced with photometric measurements; or they may be omitted, in which case the in vivo pH is calculated according to Example 4 d).

EXAMPLE 4

Figure 3:
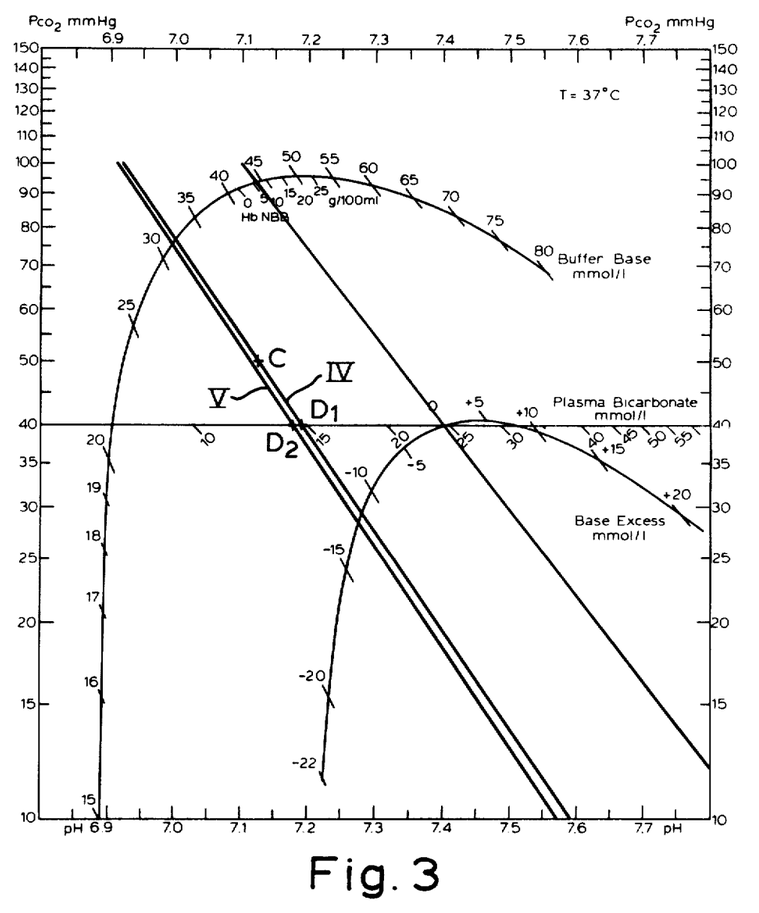

(a) Using the curve monogram shown in FIG. 3, the in vivo Base Excess line is established for a patient with the in vivo acid base status established in Example 3.

The construction of the in vivo Base Excess line IV corresponds to Example 1.

$SBE_1 = -12$ millimol/liter

"$SBB_1$" = 32 millimol/liter.

At a later time, 40 mm Hg is registered as transcutaneously measured $Pco_2$. While the patient's initial acid base status is represented by point C, the pH at the changed acid base status corresponding to the changed $Pco_2$ is 7.188 (point $D_1$). This determination is performed under the presumption that the saturation is unchanged.

It is found that the patient's saturation has also changed (that is, the transcutaneously measured $Po_2$ has changed, for example to 90 mm Hg), the changed saturation may be calculated from equations 12 and 13, using the ph 7.188:

$Sat_2 = 0.93$.

The Base Excess line V for $Sat_2 = 0.93$ can now be established, using:

$SBE_2 = SBE_1 + 0.31 \times Hb (Sat_1 - Sat_2)$  (14)

"$SBB_2$" = $SBB_2 + 0.31 \times Hb (Sat_1 - Sat_2)$  (15)

$SBE_2 = -12.5$

"$SBB_2$" = 31.5.

The Base Excess line corresponding to the changed saturation is shown as V in FIG. 3. The patient's in vivo pH on curve V (in other words at saturation 0.93) is, at the transcutaneously measured $Pco_2$ of 40 mm Hg, 7.177 (point $D_2$).

(b) The same establishments as under (a) may be performed by calculation. The calculation is illustrated in the curve monogram in FIG. 4. The starting point is the same in vivo acid base status as is used under (a).

pH = 7.122

$Pco_2 = 50$ mm Hg $Po_2 = 37.3$ mm Hg ~ $Sat_1 = 0.5$

Hb = 3.7 millimol/liter, fixed per definition.

Figure 4:
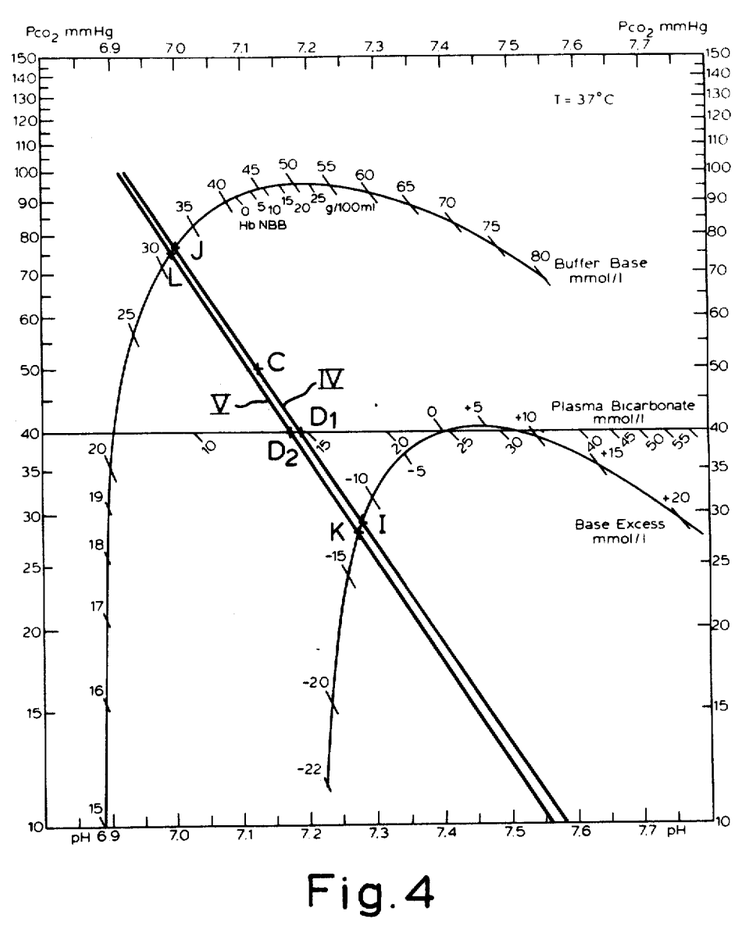

SBE may be calculated from the formulae 6, 7 and 8:

SBE = $-12.23$ millimol/liter (point I)

and

"SBB" = $41.7 + 0.68 \times$ lib + SBE = 31.99 millimol/liter (point J).

The coordinates of points I and J may be calculated from the equations 9, 10, 9', 10':

$pH_I = 7.279$ $Pco_2{}_I = 28.52$ mm Hg $pH_J = 6.998$ $Pco_2{}_J = 76.68$ mm Hg

From the coordinates for I and J, the in vivo Base Excess line IV may be calculated by means of equation 11:

$\log Pco_2 = -1.5286 \times pH + 12.5817$.

After some time, the patient's trancutaneously measured $Pco_2$ has changed to 40 mm Hg, and the corresponding in vivo pH is calculated to 7.183 (point $D_1$).

If a change in in vivo $Po_2$ to 90 mm Hg is also ascertained, Sat may be calculated from equations 12 and 13, using pH = 7.183:

$Sat_2 = 0.93$.

The Base Excess line V for $Sat_2 = 0.93$ may now be established from equations 14 and 15:

$SBE_2 = 12.72$ millimol/liter (point K).

$SBB_2 = 31.50$ millimol/liter (point L).

The coordinators are calculated as above:

$pH_K = 7.275$ $Pco_2{}_K = 27.74$ mm Hg $pH_L = 6.994$ $Pco_2{}_L = 75.49$ mm Hg

From the coordinators for K and L, the in vivo Base Excess line V may be calculated by means of equation 11:

$\log Pco_2 = -1.547 \times pH + 12.699$.

For the transcutaneously measured $Pco_2$ of 40 mm Hg, the in vivo pH will be:

In vivo pH = 7.172 (point $D_2$).

Figure 5:
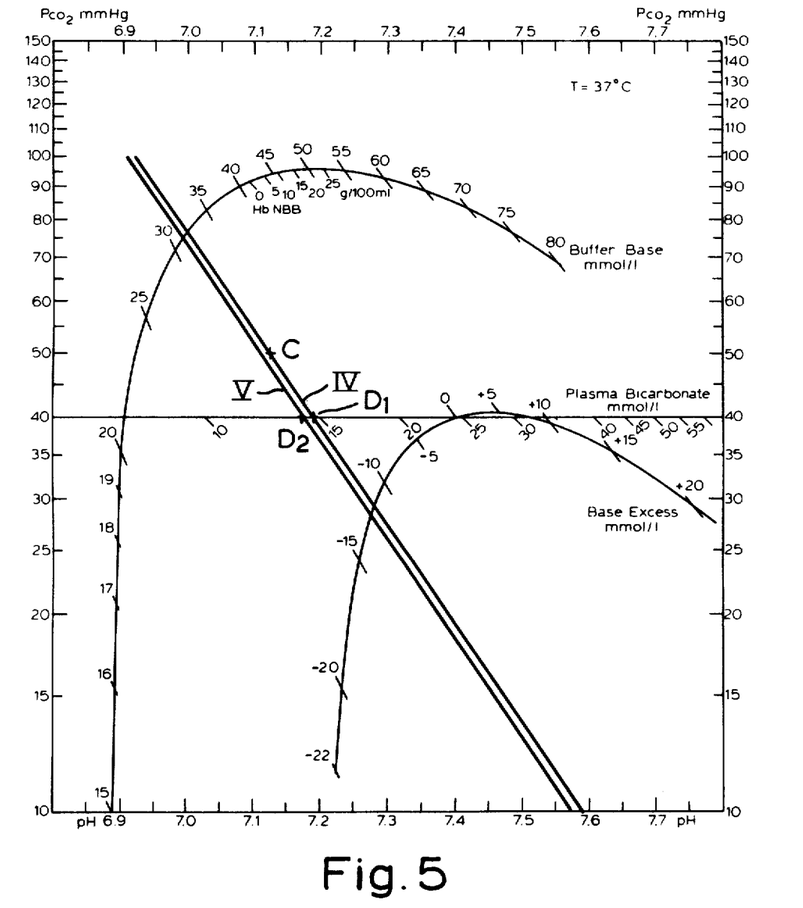

(c) The in vivo Base Excess line for a patient is calculated from the above in vivo acid base status pH = 7.122

$Pco_2 = 50$ mm Hg $Po_2 = 37.3$ mm Hg ~ $Sat_1 = 0.5$

Hb = 3.7 millimol/liter, fixed per definition (which is represented by point C in FIG. 5).

SBE may be calculated from the formulae 6, 7 and 8;

$SBE_1 = -12.2$ millimol/liter.

The slope of the Base Excess line may, with approximation, be calculated from the equation:

$$\alpha = 0.005208 \times SBE - 1.2823 - 10^{(-0.0507 \times SBE - 1.412)}$$

$$\alpha_1 = -1.507 \quad (16)$$

The Base Excess line IV is now established $$\log P_{CO_2} = \alpha_1 (pH - 7.122) + \log 50$$

pH at 40 mm $P_{CO_2}$ may now be calculated:

$$pH_{40} = 7.186$$

If the patient's in vivo $P_{CO_2}$ (transcutaneously measured $P_{CO_2}$) changes to 40 mm Hg, in vivo pH changes to In vivo pH = 7.186 (point $D_1$).

If the patient's in vivo $P_{O_2}$ changes to 90 mm Hg, Sat may be calculated from equations 12 and 13, using pH = 7.183.

$$Sat_2 = 0.93.$$

The change in SBE on change of oxygen saturation from $Sat_1$ to $Sat_2$ may be calculated from equation 14:

$$\Delta SBE = 0.31 \times Hb(Sat_1 - Sat_2) = -0.5$$

$$SBE_2 = -12.7$$

The change of $pH_{40}$ as a function of small changes in SBE may, with approximation, be calculated from the equation $$\Delta pH_{40} = 10^{(-0.01112 \times SBE_1 - 1.81487)} \quad (17)$$
$$\Delta SBE$$
$$\Delta pH_{40} = 0.010 \ (\Delta SBE = 0.5)$$

$$\Delta pH_{40\ 2} = 7.176 \text{ (point } D_2\text{).}$$

The slope of the Base Excess line for $SBE_2$ may be calculated from equation 16:

$$\alpha_2 = 1.519$$

The Base Excess line V for Sat = 0.93 is now established $$\log P_{CO_2} = \alpha_2(pH - 7.176) + \log 40$$

In vivo pH = 7.176 (point $D_2$) for $P_{CO_2}$ = 40 mm Hg and $P_{O_2}$ = 90 mm Hg.

The calculations in this example are more suited for a microcomputer with limited memory, as these calculations do not require that the BE and the BB curves have been read into the computer.

(d) In vivo Base Excess line is calculated from the same in vivo acid base status as above, but disregarding saturation.

pH = 7.122

$P_{CO_2}$ = 50 mm Hg $P_{O_2}$ = 37.3 mm Hg ~ $Sat_1$ = 0.5

HB = 3.7 millimol/liter, fixed per definition.

Figure 6:
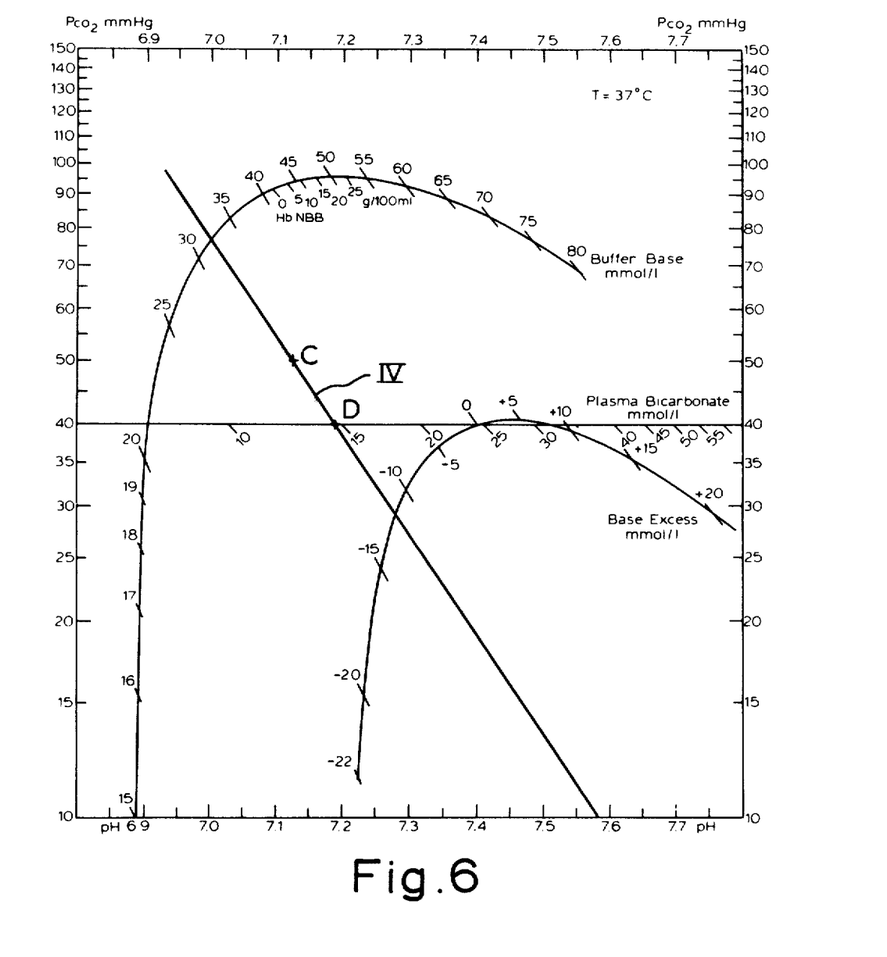

The calculation is illustrated by the curve monogram in FIG. 6.

The conditions are here additionally simplified as it has been found that the Base Excess lines for a given Hb with approximation intersect in one point.

Hb = 3.7 millimol/liter. (Intersection (pH, log $P_{CO_2}$) = (5.66, 3.91)).

The Base Excess line IV is hereby established to $$pH = \frac{(5.66 - 7.122)}{3.91 - \log 50} (\log P_{CO_2} - \log 50) + 7.122 \quad (18)$$

If the transcutaneously measured $P_{CO_2}$ changes to 40 mm Hg, pH changes to:

In vivo pH = 7.186 (point D).

I claim:

1. A method for continuous or intermittent monitoring of a patient's in vivo plasma pH value, comprising establishing the patient's acid base status with performance of at least one in vitro determination on a blood sample withdrawn from the patient, and thereafter determining the patient's in vivo plasma pH on the basis of the thus established initial acid base status and on the basis of continuously or intermittently registered results of a non-invasive measurement of the patient's actual blood $P_{CO_2}$.

2. A method according to claim 1, comprising establishing the patient's initial acid base status with performance of an in vitro determination of pH and $P_{CO_2}$ on an arterial or capillary blood sample withdrawn from the patient and transferred anaerobically.

3. A method according to claim 1, comprising establishing the patient's initial acid base status with performance of in vitro determination of pH on an arterial or capillary blood sample withdrawn from the patient and transferred anaerobically and on the basis of the result of a non-invasive measurement of the patient's blood $P_{CO_2}$ performmed simultaneously with the withdrawal of the blood sample.

4. A method according to claim 2, comprising calibrating the in vivo $P_{CO_2}$ measuring equipment on the basis of the result of the in vitro $P_{CO_2}$ measurement and on the basis of the result of a non-invasive measurement of the patient's blood $P_{CO_2}$ performed simultaneously with the withdrawal of the arterial blood sample.

5. A method according to claim 2, comprising additionally performing, on the anaerobically transferred arterial or capillary blood sample, a determination of the oxygen saturation, or registering the result of a non-invasive oxygen saturation determination performed simultaneously with the blood sample withdrawal, and including, in the determinations of the patient's in vivo plasma pH for a period thereafter, the result of non-invasive oxygen saturation determinations performed at the actual times.

6. A method according to claim 1, comprising establishing the patient's initial acid base status with performance of in vitro determination of pH, $P_{CO_2}$ and an additional blood parameter, said additional blood parameter being selected from the group consisting of the hemoglobin content and another blood parameter which is a function of the hemoglobin content, on a non-anaerobically transferred blood sample withdrawn from the patient, and on the basis of the result of non-invasive measurement of the patient's blood $P_{CO_2}$ performed simultaneously with the withdrawal of the blood sample.

7. A method according to claim 6, comprising additionally performing, on the blood sample, an oxygen saturation determination and registering the result of a non-invasive oxygen saturation determination performed simultaneously with the withdrawal of the blood sample, any differences between the oxygen saturation determination and the result of the non-invasive oxygen saturation determination being used to correct the initial acid base status; and in the determinations of the patient's in vivo plasma pH performed for a period thereafter, including the results of non-invasive oxygen saturation determinations performed at the actual times.

8. An apparatus for continuous or intermittent monitoring of a patient's in vivo plasma pH, comprising a first input means (13a; 20a) for signals representing results of a non-invasive $P_{CO_2}$ measurement and a second input means (25a; 27a) for introduction of at least one blood parameter determined by in vitro measurement, a pH registration unit (12; 12a), a conversion means 21, said pH registration unit being connected to the first input means (13a; 20a) through the conversion means (21), the conversion means (21) being adapted to perform the conversion of the received $P_{CO_2}$ signals to pH units as a function of a parameter set read into the conversion means (21), and representing an initial acid base status, the said parameter set comprising at least one blood parameter determined by in vitro measurement introduced via the second input means (25a; 27a).

9. An apparatus according to claim 8, comprising a means (24; 26) for introducing at least one blood parameter determined in vitro, said means for introducing at least one blood parameter determined in vitro (24; 26) being connected to the second input means (25a; 27a).

10. An apparatus according to claim 9, in which the means (24; 26) for introduction of at least one blood parameter determined in vitro is a keyboard.

11. An apparatus according to claim 9, in which the means (24; 26) for the introduction of at least one blood parameter determined in vitro is pH measuring equipment.

12. An apparatus according to claim 9, in which the means (24; 26) for introduction of at least one blood parameter determined in vitro is blood gas equipment.

13. An apparatus according to claim 8, which in addition to the pH registration unit (12; 12a) comprises a $P_{CO_2}$ registration unit (15) connected to the first input means (13a; 20a) for signals representing the result of a non-invasive $P_{CO_2}$ measurement.

14. An apparatus according to claim 8, comprising a third input means (14a) for signals representing the result of a non-invasive $P_{O_2}$ measurement or a non-invasive oxygen saturation measurement, said signals representing the result of a non-invasive $P_{O_2}$ measurement or a non-invasive oxygen saturation measurement being at least a part of the parameter set, the said third input means communicating with the conversion means (21).

15. An apparatus according to claim 12, and comprising $P_{O_2}$ registration unit (16) communicating with the said third input means (14a).

16. An apparatus according to claim 1, comprising a synchronization means (28; 29), at the activation of which the non-invasively measured $P_{CO_2}$ value registered at the activation time and optionally the non-invasively measured $P_{O_2}$ value registered at the activation time is/are stored in the conversion means (21).

* * * * *